United States Patent [19]

Heitman et al.

[11] 4,313,349

[45] Feb. 2, 1982

[54] SEALED ELECTRICAL CONTROL DEVICE FOR X-RAY APPARATUS

[75] Inventors: Christopher J. Heitman, Milwaukee; Joseph A. Becker, Waukesha, both of Wis.

[73] Assignee: General Electric Company, Schenectady, N.Y.

[21] Appl. No.: 109,022

[22] Filed: Jan. 2, 1980

[51] Int. Cl.³ .............................................. G05G 1/04
[52] U.S. Cl. ........................................ 74/507; 74/98; 74/384; 74/491; 74/531; 74/566; 74/406; 338/67
[58] Field of Search ................. 74/523, 566, 395, 405, 74/406, 409, 411, 491, 531, 507, 10.8, 98, 384; 338/67, 118, 128

[56] References Cited

U.S. PATENT DOCUMENTS

| | | | |
|---|---|---|---|
| 2,373,225 | 4/1945 | Clickner | 74/531 |
| 3,183,726 | 5/1965 | Badger | 74/406 |
| 3,208,299 | 9/1965 | Leonard et al. | 74/491 |
| 3,251,238 | 5/1966 | Fuqua | 74/491 |
| 3,748,923 | 7/1973 | Babbit, Jr. et al. | 74/566 |

*Primary Examiner*—Kenneth Dorner
*Attorney, Agent, or Firm*—Ralph G. Hohenfeldt

[57] ABSTRACT

A control device has a fixedly mountable frame which has recesses and a fixed shaft extending across the recesses. Flat sided spherical elements having manual levers extending from them are rotatable on the shaft and each element has a sector gear fastened to one of its flat sides. Flat springs extend from the frame and press on the spherical elements to develop friction. Potentiometer support brackets are pivotally mounted to shoulders on the flat springs. Each potentiometer shaft has a spur gear which meshes with a sector gear. The spur gears and sector gears are biased into meshing relation with coil springs that span between brackets. A lip seal is provided between the spherical elements and their housing.

5 Claims, 5 Drawing Figures

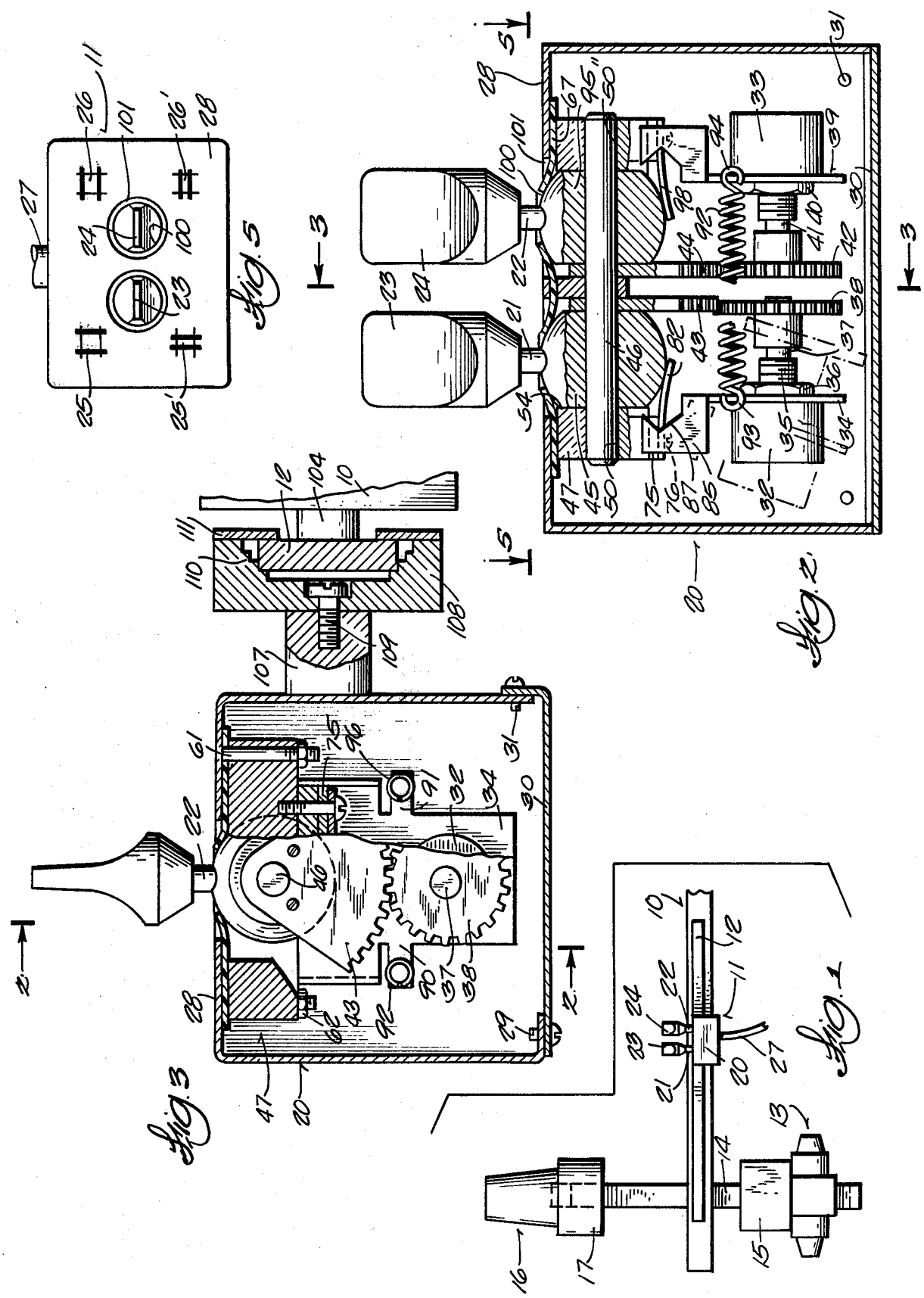

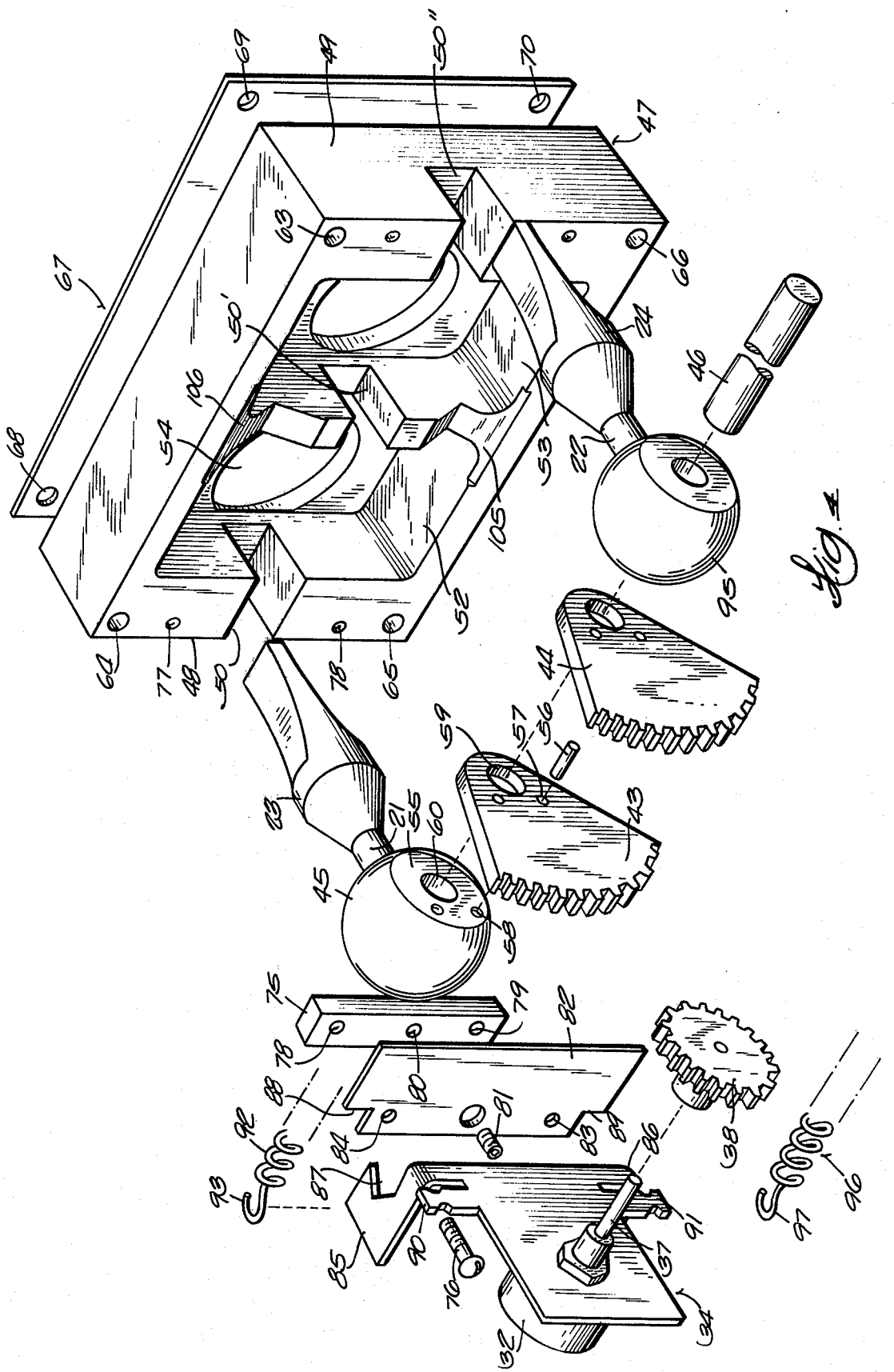

4,313,349

SEALED ELECTRICAL CONTROL DEVICE FOR X-RAY APPARATUS

This invention pertains to a sealed electrical control device which has a variety of applications but is especially useful to control the x-ray beam collimator in an x-ray cardiovascular catheterization system. Operation and use of the device will be exemplified herein in connection with such system.

Heart catheterization involves advancing a catheter through a blood vessel to the heart while progress of the catheter tip is observed on the video display screen of an x-ray fluoroscopic system. The catheterization apparatus comprises an x-ray transmissive patient supporting table which has an x-ray source and associated beam collimator on one side of it and an x-ray image receptor such as an electronic image intensifier on the other side. The collimator has pairs of blades which are movable crosswise of each other to define the boundaries of the x-ray beam and observation field and to intercept radiation outside of this field so that the patient does not receive any unnecessary radiation dosage.

A control device incorporating manually operable potentiometers has been used customarily to provide operator input to the servo system electronics which controls the motors that position the collimator blades in response to changes in potentiometer settings. Because the control device must be mounted at tableside for convenience of the operating physician, the device should be sealed against fluids such as blood which may be spilled incidental to insertion of a catheter in a blood vessel. The lack of good seals against invasion by fluids such as blood and cleaning solutions has been one of the deficiencies in prior art control devices.

Another problem with prior art control devices is that they are difficult to operate through the sterile sheet which customarily covers most of the patient, the table and control device during a catheterization procedure. A requirement of a good control device is that the user should be able to operate one or the other pairs of collimator blades or both pairs simultaneously without being distracted from the main event of catheterization by being required to focus too much attention on manipulating the control device.

Another problem in prior art control devices has been the presence of too much free play and backlash in the mechanism which couples the operator control levers to the potentiometers. This is manifested in overtravel or undertravel of the blades and requires corrective resettings which are distracting to the physician who observes the x-ray field set by the collimator blades on the video display screen.

SUMMARY OF THE INVENTION

Objects of the present invention are to provide a control device that overcomes the above-noted disadvantages and that is structurally simple, is easy to assemble, affords easy adjustment and zero position setting of the potentiometers, is self-compensating for wear, has no backlash or free play, is easy to clean, is sealed against entry of fluids and that permits the potentiometer control levers to be grasped and operated simultaneously or independently.

In general terms, the illustrative embodiment of the new control device comprises a housing which has holes in one of its walls. A chassis member or frame is fastened in the housing and it has cavities which align with the apertures. There is an oblate spherical element in each cavity and each spherical element has a manually operable lever extending from it and through the housing opening. A pliant sheet that has holes through which the levers extend is captured between the frame and housing wall and the margins of the holes form lip seals by interfacing with the spheres. The spherical elements are mounted for turning on a shaft that is fixed in the frame. Each spherical element has a sector gear fastened to its flat side. The potentiometers have a spur gear on their shafts. The sector gears meash with the spur gears. Flat springs are mounted on the frame and their ends press on the spherical elements to provide a frictional force for maintaining the spheres in the rotational positions in which they are manually set. The potentiometers are mounted on brackets which, in turn, are pivotally mounted on the flat springs and are held in place under the influence of tensioned coil springs which force the spur gears into good meshing relation with the sector gears. The brackets can be pivoted manually in opposition to the force of the coil springs to unmesh the spur gear and allow it to be rotated for turning the potentiometer shaft to the initial or zero setting position for the potentiometer.

How the foregoing and other more specific objects of the invention are achieved will appear in the ensuing more detailed description of its which will now be set forth in reference to the drawings.

DESCRIPTION OF THE DRAWINGS

FIG. 1 is a diagram of a part of a cardiovascular x-ray examination table system for illustrating how the new control device may be used;

FIG. 2 is a front elevation view of the device, partly in section, where the section is taken along the offset section line 2—2 in FIG. 3;

FIG. 3 is an end elevation view of the device, partly in section, where the section is taken along the line 3—3 in FIG. 2;

FIG. 4 is a partial exploded view of the control device; and

FIG. 5 is a plan view of the housing which is occupied by the new control device.

DESCRIPTION OF A PREFERRED EMBODIMENT

FIG 1 is a diagram of an x-ray cardiovascular examination system in which the new control device is used for controlling the x-ray field collimator blades. In this figure, the x-ray transmissive table top on which a patient would be supported supinely during an examination is shown fragmentarily and indicated by the reference numeral 10. The new control device is generally designated by the numeral 11 and it is shown as being mounted at tableside on an equipment mounting bar 12. An x-ray tube casing 13 having an x-ray tube, not shown, inside is supported on an arm 14. A conventional collimator appearing as a box 15 contains orthogonally arranged pairs of collimator blades, not visible, which are movable toward and away from each other for defining the shape of the x-ray beam which is projected through the table 10 and a patient thereof. An x-ray image intensifier 16 is supported on arm 14 on the side opposite of the x-ray table top from the x-ray source 13. The x-ray image input face of the intensifier is at its bottom 17.

The collimator blade control device 11 is in a metal housing 20. A pair of operating levers 21 and 22 extend from the housing and each lever has a manually engageable knob 23 and 24. Levers 21 and 22 are movable toward and away from the observer in FIG. 1 to effectuate adjustment of the pairs of collimator blades within collimator box 15. The collimator blades are driven by a servo motor system, not visible, in response to analog voltage signals generated by rotating potentiometers in the control device in response to actuation of levers 21 and 22. The potentiometers are part of the control device and will be described in greater detail shortly.

In FIG. 5, the top view of the control box shows that it is provided with representations of the longitudinally movable pair of collimator blades 25 and 25' and the laterally movable pair 26 and 26'. When control knob 23 is grasped and pushed forward away from the observer in FIG. 5, the longitudinally movable collimator blades separate as indicated by the blade representations being separated in diagram 25. When knob 23 is pulled toward the observer in FIG. 5, the longitudinally movable blades close as indicated by their representation 25'. The other knob 24 on lever 22 is pushed to open the laterally movable collimator blades as indicated by the diagram 26 and is pulled to close these blades as indicated by the diagram 26'. A fragment of the electrical cable 27 is also shown extending out of the control housing in FIG. 5.

The control device will now be described in greater detail in reference to FIGS. 2, 3 and 4.

FIG. 2 shows the control device assembled in its housing 20 which has an access plate 30 at its bottom that is secured to the housing by means of machine screws 29 and 31. In this embodiment, the control device has two potentiometers 32 and 33 mounted in it. It is these potentiometers which are turned by actuation of levers 21 and 22 to produce analog signals to the collimator servo motor electronics, not shown, so as to adjust the collimator blade openings. Typical potentiometer 32 is secured to a pivotal bracket 34 which will be described in detail later. The potentiometer has a threaded stem 35 for fastening it to the bracket by means of a nut 36. The potentiometer has a shaft 37 on which a spur gear 38 is fixed. Rotation of spur gear 38 results in rotation of the wiper in potentiometer 32 and causes variations in its analog output voltage.

The other potentiometer 33 is similarly mounted on a bracket 39 by means of a nut 40. The shaft 41 of this potentiometer also has a spur gear 42 fastened to it. Spur gears 38 and 42 are meshed with gear sectors 43 and 44, respectively, as can be seen in FIG. 2. The manner in which typical spur gear 38 meshes with typical sector gear 43 is also clearly evident in FIGS. 3 and 4. Sector gear 43 is pinned to the flat side of a generally spherical element 45 which is rotatable on a shaft 46 which is fixed in a chassis or frame 47. Sector gear 44 for driving spur gear 42 and the second potentiometer 33 is pinned to a spherical element 95 which is also rotatable on shaft 46.

The details of frame 47 may be seen in the FIG. 4 exploded view. The end walls 48 and 49 of the frame are provided with slots 50, 50' and 50" into which the opposite ends of shaft 46 fit. Frame 47 is provided with a pair of recesses 52 and 53. Taking sphere 45 as an example, it fits into recess 52 such as to permit a part of its spherical periphery to extend through a hole 54 in the top of frame 47. This is evident in FIGS. 2 and 3 as well. Referring again to FIG. 4 spherical element 45 is essentially an arc of revolution or an oblate spheroid which has two flat sides one of which 55 is visible. Sector gear 43 interfaces with flat side 55 and is secured to it by means of pins one of which is shown in FIG. 4 and is marked 56. These pins fit through holes 57 in sector 43 and into holes 58 in spherical element 45. Sector gear 43 has a hole 59 and spherical element 45 has a hole 60 which allows the pinned together spherical element and sector gear to rotate on stationary shaft 46 which, in this embodiment, is clamped in aligned frame slots 50, 50' and 50" as will be explained later.

Referring to FIG. 3, one may see how the frame 47 is fixed to the top of housing 20 by means of four stud bolts, two of which, 61 and 62, are visible in FIG. 3. These studs may be welded or pressed fit and peened into appropriate holes in the top of housing 20. The four holes in frame 47 through which the studs fit are marked 63–66 in FIG. 4. As can be seen in this figure, on one side of frame 47 there is a pliant sheet 67 which may be made of neoprene rubber, for example, and which serves as a lipseal for the spherical elements as will be discussed in greater detail later. Sheet 67 has four holes in its corner regions, three of which 68, 69 and 70 are visible in FIG. 4. These holes in sheet 67 are congruent with holes 63–66 in frame 47 so that the sheet and frame can be fit over studs 61 and 62 and its other matching pair which are not visible but have self-evident locations.

As can be seen in FIG. 4, and in FIG. 2 as as well, clamping bars such as the one marked 75 are used to hold down shaft 46 in aligned frame recesses 50, 50' and 50". Bar 75 interfaces with end wall 48 of frame 47 and is held there with a pair of screws such as the one marked 76 in FIG. 4. Screws 76 turn into threaded holes 77 and 78 in the frame member. To permit this, clamping bar 75 is provided with a pair of holes 78 and 79 through which screws 76 fit. The clamping bar also has a central hole 80 which has an internal thread and receives a socketed set screw 81 which holds down shaft 46 in slot 50.

As shown in FIG. 4 and as can also be seen in FIG. 3, screws 76 also hold down a flat phosphor-bronze spring member 82 whose outer end presses against spherical element 45 to impose a frictional force on the spherical element which maintains it in whatever rotational position the user sets it by actuation of operating lever 21. Flat spring 82 has a central hole through which set screw 81 may be inserted so it can be threaded into hole 80 in clamping bar 75 for clamping shaft 46. Flat spring 82 also has a pair of holes 83 and 84 through which the shanks of screws 76 pass so flat spring 82 and clamping bar 75 may be held down jointly with screws 76. Flat spring 82 will maintain a constant frictional force on spherical element 45 even if there is some wear in the relatively movable parts after extended use of the control device in which case the feel of the operating levers will always be the same to the user.

As was previously mentioned when FIGS. 2 and 3 were being discussed, a typical potentiometer 32 is mounted on a bracket 34 which can be seen best in FIG. 4. Bracket 34 has a pair of wings one of which, 85, is visible in FIG. 4. The other wing is concealed from view but is similarly shaped and is located near where the reference numeral 86 is applied. Typical wing 85 is provided with a v-shaped notch 87. This notch is for pivotally mounting bracket 34 on flat spring 82. For this purpose, flat spring 82 is provided with shoulders 88 and 89 onto which the notches such as the one marked 87 fit to effect a pivotal connection between bracket 34 and flat spring 82. Bracket 34 for potentiometer 32 and similar bracket 39 for potentiometer 33 are held in place with springs as will be explained next.

Bracket 34 is provided with a pair of tabs 90 and 91 as can be seen in FIG. 4 which are for enabling the bracket to be biased pivotally with a pair of tensioned coil springs 92 and 96 which are shown fragmentarily in FIG. 4. Coil springs 92 and 96 have hook-shaped ends 93 and 97 which hook onto tabs 90 and 91 on bracket 34 and tend to pivot the bracket on flat spring shoulders 88 and 89. However, pivotal movement is limited by the fact that spur gear 38 becomes meshed compressively into sector gear 43. The advantage of this construction is that no free play can ever develop between the teeth of spur gear 38 and sector gear 43 so that the potentiometer shaft 37 will always track operating lever 21 accurately. Any wear that might occur between sector gear 43 and spur gear 38 is compensated by further pivoting of bracket 34 under the influence of spring 92.

As can be seen in FIG. 2, the springs have their opposite ends attached to the other pivotal bracket 39 on which the other potentiometer 33 is mounted. Spring 92, as can be seen in this figure, has a hook 94 at its other end which engages with a tab on bracket 39 so that the spur gear 42 is driven into good meshing relationship with the teeth on the other sector gear 44. Spring 96 is not visible in FIG. 2 but is similarly attached to bracket 39. Sector gear 44 is, of course, mounted on an oblate or flat-sided spherical element 95 through which potentiometer 33 is operated. Spherical element 95 is also pressed by a flat spring 98. The operating mechanism for potentiometer 33 is similar to the mechanism which has been described for operating potentiometer 32 and its structure and function is considered to be self-evident so it will not be described in detail.

Another advantage of having the potentiometer supporting brackets such as the typical one 34 pivotal is that spur gear 38 may be swung out of meshing relationship with sector gear 43 in opposition to the force of tensioned coil springs 92 and 96. Unmeshing allows the spur gear and hence potentiometer shaft 37 to become rotatable by manually turning it with the use of the fingers of the spur gear. This allows the potentiometer to be set to a zero position or one of its home positions conveniently to assure that it will be coordinated with operating lever 21 when it is in its zero or home position at one end of its travel or the other. In prior designs, parts had to be dissassembled in order to make initializing potentiometer adjustments. The phantom line representation of potentiometer 32 and its bracket 34 illustrates how it pivots to an angular position on the shoulders of flat spring 82. Another feature of the control device is the manner in which it is sealed in its housing 20. This can be seen best FIGS. 2 and 3. The pliable sealing sheet 67 shown in FIG. 2 has been mentioned previously. In this figure one may see that sealing sheet 67 is captured compressively between the top of frame 47 and the inside of the housing 20 top wall 28. As can be seen in FIG. 2 sheet 67 has two holes in it, a typical one of these holes is marked 100 and lever 22 of spherical element 95 extends through hole 100. The margin of the sheet surrounding the hole is in contact with the curved surface of spherical element 95 and the margin is deflected to produce good sealing contact. The wall 28 of housing 20, of course, has a hole 101 which allows the curved surface of spherical element 95 to bulge outwardly to effect deflection of the sheet 67 when the frame 47 is clamped on the studs 61, 62 and the like against the inside of the housing top wall 28.

Hole 100 is large enough to allow operating lever 22 to travel from one angular limit to another without abutting the edge of the hole. The other spherical element 45 is similarly sealed by means of perforated sheet 67 and it is deemed unnecessary to describe it. One may see the margin of hole 100 in FIG. 5 which also shows how the hole 101 in the housing top wall 28 allows a small lipseal annulus of the pliable sheet to appear on top of the housing.

Another feature of the new control device is that the stops for the operating levers 21 and 22 may be fixed instead of being adjustable to obtain precision that is built into the device in the factory. Referring to FIG. 4, the stops are constituted by a pair of beveled surfaces 105 and 106 which are formed in frame 47. These beveled surfaces are in alignment with sector gears 43 and 44. The edges of the sector gears abut these stop surfaces to establish travel limits for both operating levers 21 and 22 in both directions.

Earlier, while discussing FIG. 1, it was mentioned that the control device 11 is conveniently mountable on a bar 12 which is fixed to the x-ray table top 10. The details of the device mounting means are more clearly shown in FIG. 3. Here it is shown that bar 12 is supported on posts 104. A bracket 107 extends from one side of the control device housing 20. Bracket 107 has a multiple channeled member 108 fastened to it by means of scres such as the one marked 109. The channel in member 108 has stepped sides 110 which, as should be readily apparent, allows it to fit complementarily with a variety of different sized bars 12. This makes it convenient to attach the device to other x-ray tables or medical apparatus which have differently sized bars for holding accessories. The channel member is retained on bar 12 with flat straps 111 which overlay the edges of the bar and are held onto the channel member with screws that are not shown.

It should be understood that the potentiometer controlling levers can be used singly or in pairs as illustrated, or in numbers of pairs in the same housing if desired. When a potentiometer or other electrical component and the described mechanism for operating it is used singly, one end of the spring which biases the potentiometer support bracket would simply have to be attached to a fixed point instead of to a tab on an adjacent potentiometer bracket as in the illustrated embodiment.

Although a preferred embodiment of the new control device has been described in considerable detail, such description is intended to be illustrative rather than limiting, for the invention may be variously embodied and is to be limited only by interpretation of the claims which follow.

We claim:

1. A device for controlling an x-ray beam collimator comprising:
   a frame member for being mounted in a fixed position,
   an element having a spherical surface, said element being supported from the frame member for rotation relative to said member and a manually engageable lever extending from said element for rotating said element,
   first gear means rotatable with said spherical element about the rotational axis of said element,
   pivotally mounted bracket means and a potentiometer mounted on said bracket means, said potentiometer having an operating shaft extending from it, second gear means fastened to the potentiometer shaft for meshing with said first gear means when said pivotal bracket means is in one of its angular positions and for being unmeshed when said bracket means is in other of its angular positions, spring means for urging said bracket means into a position where said gear means are caused to mesh, a wall member on which said frame member is supported, said wall member having a hole into which the spherical surface of said element protrudes and through which said operating lever extends, and a pliant generally planar element interposed between said frame member and wall member, said pliant element having a hole through which said lever extends and which provides a marginal region around said hole that is deflected by said protruding spherical surface to form a lip seal therewith.

2. A device for cntrolling an x-ray beam collimator comprising:

a wall member having spaced apart holes, a frame member having holes which are alignable, respectively, with said holes in the wall member and means for fastening said frame member to one side of said wall member with said holes in said frame member and wall member aligned, shaft means mounted to said frame member and spaced from its holes, elements which have a spherical surface mounted for rotation about the axis of said shaft means, said spherical surfaces protruding, respectively, into said aligned holes, manually engageable lever means extending from the respective spherical elements through said aligned holes to enable rotation of said elements from the other side of said one side of said wall member, a sector gear fastened to each spherically surfaced element for rotation with said element about the axis of said shaft means, a plurality of pivotally mounted bracket means and potentiometers mounted on the respective bracket means, each of said potentiometers having an operating shaft extending from it and said shafts each having a spur gear for meshing, respectively, with said sector gears when said brackets are in one of their angular positions and for unmeshing when said bracket means are pivoted to other of their angular positions, spring means for biasing said bracket means into positions where said respective spur gears and sector gears are caused to mesh, and sealing means for effecting a seal between said wall means and spherical surfaces of said elements, respectively, comprising a sheet of pliant material interposed between said frame member and said wall member and having holes aligned with said wall member holes and frame member holes, said sheet providing marginal regions around its holes that are deflected by said protruding spherical surfaces, respectively, to form lip seals therewith.

3. A device for controlling an x-ray beam collimator comprising:

a wall member having spaced apart holes, a frame member having holes which are alignable, respectively, with said holes in the wall member and means for fastening said frame member to one side of said wall member with said holes in said frame member and wall member aligned, shaft means mounted to said frame member and spaced from its holes, elements which have a spherical surface mounted for rotation about the axis of said shaft means, said spherical surfaces protruding, respectively, into said aligned holes, manually engageable lever means extending from the respective spherical elements through said aligned holes to enable rotation of said elements from the other side of said one side of said wall member, a sector gear fastened to each spherically surfaced element for rotation with said element about the axis of said shaft means, a plurality of pivotally mounted bracket means and potentiometers mounted on the respective bracket means, each of said potentiometers having an operating shaft extending from it and said shafts each having a spur gear for meshing, respectively, with said sector gears when said brackets are in one of their angular positions and for unmeshing when said bracket means are pivoted to other of their angular positions, spring means for biasing said bracket means into positions where said respective spur gears and sector gears are caused to mesh, sealing means for effecting a seal between said wall means and spherical surfaces of said elements, respectively, and, a plurality of flat springs mounted to said frame member and extending into contact relation with the spherical surfaces of said elements, respectively, to prevent said elements from rotating freely.

4. The device as in claim 3 wherein said pivotal mounting of said brackets is achieved by providing said brackets with notches which engage with edges of said flat springs, respectively.

5. The device as in any of claims 2, 3 or 4 wherein said spring means which bias said bracket means are coil springs attached at their opposite ends to the bracket means, respectively, for supplying a biasing force simultaneously to a pair of bracket means.

* * * * *